(12) United States Patent
Sieckmann

(10) Patent No.: US 7,760,428 B2
(45) Date of Patent: Jul. 20, 2010

(54) SPECIMEN SLIDE UNIT FOR HOLDING A SPECIMEN THAT IS TO BE EXAMINED UNDER A MICROSCOPE OR ANALYZED WITH A LABORATORY ANALYSIS SYSTEM

(75) Inventor: Frank Sieckmann, Bochum (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 273 days.

(21) Appl. No.: 11/570,488

(22) PCT Filed: Jun. 10, 2005

(86) PCT No.: PCT/EP2005/052702

§ 371 (c)(1),
(2), (4) Date: Dec. 12, 2006

(87) PCT Pub. No.: WO2005/121865

PCT Pub. Date: Dec. 22, 2005

(65) Prior Publication Data

US 2007/0279735 A1    Dec. 6, 2007

(30) Foreign Application Priority Data

Jun. 12, 2004  (DE) ............... 10 2004 028 286
Jun. 29, 2004  (DE) ............... 10 2004 031 570

(51) Int. Cl.
*G02B 21/26* (2006.01)
(52) U.S. Cl. .................. 359/391; 359/368
(58) Field of Classification Search ............ 359/368, 359/391
See application file for complete search history.

(56) References Cited

U.S. PATENT DOCUMENTS 5,561,556 A * 10/1996 Weissman ............... 359/396
6,967,573 B1 * 11/2005 Murdoch et al. ............ 340/505
2002/0008140 A1     1/2002 Reynolds et al.
2002/0030598 A1 *  3/2002 Dombrowski et al. ..... 340/572.1
2004/0212500 A1 * 10/2004 Stilp ......................... 340/541
2004/0257601 A1 * 12/2004 Tomiyasu et al. ............ 358/1.9

FOREIGN PATENT DOCUMENTS

| DE | 19544054 A1 | 5/1997 |
| DE | 197 36 470 | 3/1999 |
| DE | 299 06 382 | 9/1999 |
| DE | 19853407 | 5/2000 |
| DE | 100 10 140 | 9/2001 |

(Continued)

OTHER PUBLICATIONS

"Barcode aufgepasst! Neue RFID-Chips von Infineon lesen 500 intelligente Etiketten gleichzeitig aus", press release (BoxID 13724), 'Online!' Dec. 2, 2003, XP002342294.

(Continued)

*Primary Examiner*—Joshua L Pritchett
(74) *Attorney, Agent, or Firm*—Leydig, Voit & Mayer, Ltd.

(57) ABSTRACT

A specimen slide unit for holding a specimen that is to be examined under a microscope or analyzed with a laboratory analysis system includes a specimen slide, a data carrier device and a signal element. The data carrier device has a radio frequency identification tag that can be read out and/or written on using Phase Jitter Modulation so as to switch a communication carrier frequency between two predefinable communication carrier frequencies. The signal element can be activated so as to assist an operator in following a predefinable processing sequence including a second specimen slide unit when the RFID tag is in a range of action of the read/write device. The signal element can be a visual or an acoustic signal element.

12 Claims, 2 Drawing Sheets

FOREIGN PATENT DOCUMENTS

| | | |
|---|---|---|
| DE | 10161302 | 7/2003 |
| DE | 10240814 A1 | 3/2004 |
| DE | 102 51 132 | 5/2004 |
| GB | 2 379 739 | 3/2003 |
| JP | 2004125788 A | 4/2004 |
| WO | WO-99/34526 | 7/1999 |
| WO | WO-2005121865 | 12/2005 |

OTHER PUBLICATIONS

International Preliminary Report on Patentability, PCT/EP2005/052702, mailed Jan. 11, 2007.

Klaus Finkenzeller, "RFID Handbuch" (RFID Handbook), published by Carl Hanser Verlag München Wien, $2^{nd}$ edition, Munich, Germany 2000, chapter 1 and 2.

* cited by examiner

SPECIMEN SLIDE UNIT FOR HOLDING A SPECIMEN THAT IS TO BE EXAMINED UNDER A MICROSCOPE OR ANALYZED WITH A LABORATORY ANALYSIS SYSTEM

CROSS REFERENCE TO PRIOR APPLICATION

This is a U.S. national phase application under 35 U.S.C. §371 of International Patent Application No. PCT/EP2005/052702, filed Jun. 10, 2005, and claims benefit of German Patent Application Nos. 10 2004 028 286.2, filed Jun. 12, 2004, and 10 2004 031 570.1, filed Jun. 29, 2004, which are incorporated by reference herein. The International Application was published in German on Dec. 22, 2005 as WO 2005/121865 A1 under PCT Article 21(2).

The present invention relates to a specimen slide unit to hold a specimen that is to be examined under a microscope or analyzed with a laboratory analysis system. The specimen slide unit comprises a specimen slide that holds the specimen and a data carrier device. The data carrier device can be read out and/or written on in a contact-free manner by a read/write device. Moreover, the present invention relates to a read/write device for reading out and/or writing on a specimen slide unit, to communication and/or data transmission software, to a microscope with which a specimen associated with a specimen slide unit can be examined, to a container to hold at least one specimen slide and/or at least one specimen slide unit, to a method for examining a specimen under a microscope and/or for analyzing a specimen with a laboratory analysis system and to the use of a specific data carrier device for a specimen slide that is used for microscopic analysis and/or for analysis with a laboratory analysis system. Specimen slide units as set forth in the present invention are not only slides made of glass, but can also be Petri dishes, biosensors, bio-chips or microtiter plates

BACKGROUND

Specimen slide units are known from the state of the art. Thus, for example, specimen slide units are known in the form of conventional slides made of glass onto which the specimen to be examined under a microscope is mounted. A laboratory analysis system comprises, for instance, numerous processing and analysis devices, wherein the specimen slide units are transferred manually or automatically from one processing or analysis device to another. The specimens can likewise be processed or analyzed manually or automatically.

A specimen slide unit made of glass normally has a labeling field on which a marking can be applied with which the specimen located on the specimen slide can be labeled, thus making it identifiable. In the simplest case, relevant information is written manually on the labeling field, meaning that the labeling field is a kind of storage device or data carrier device. However, it is difficult to add additional information to this type of marking, since the marking surface area available for labeling on the specimen slides is small and limited. Moreover, the legibility of the marking is often impaired since the writing on the specimen slide can be smeared or the writing can be unclear. If the specimen slides have to be stored for several years to serve as court evidence, for example, in forensic technology, in scientific expert opinions or in pathological examinations, handwritten marking of the specimen slides is not suitable since it is likely that the labeling will be destroyed as the years go by.

The specimen slides can also be labeled by means of barcodes. The barcode applied onto the specimen slide constitutes the data carrier device that can be read out by a barcode reader. Since the amount of information that can be stored on a one-dimensional barcode depends especially on its length or, in the case of a two-dimensional barcode, on its surface area, and since only short barcode lengths are possible because of the limited space available on a conventional specimen slide, the amount of data that can be stored on a specimen slide in this manner is limited. Moreover, the stored information cannot be subsequently changed unless the barcode is destroyed.

German patent application DE 100 10 140 A1 describes a device for handling and/or processing specimens, preferably automatically, in which the specimens are taken to a processing station by means of a specimen slide and, after having been processed, are taken away from there. The specimen slide of DE 100 10 140 A1 can comprise an electric storage medium in which specimen information can be stored. The electric storage medium can have a transponder. Consequently, this constitutes contact-free data transmission between a storage medium, for example, an EPROM component, and a read/write device, whereby this data had previously been stored in the storage medium. For purposes of reading out the information, the energy needed by the transponder, which usually functions passively, is generated inductively by the read/write device. Hence, a transponder unit consists at least of one coil and of the storage medium.

The read-out speed is relatively slow so that a transponder has to be present in the range of action of the read/write device for at least an appropriate time span. If several transponders are simultaneously present in the range of action (detection area) of a read device, then the transponder data will be read out erroneously since an unambiguous identification that is not influenced by other transponders is not possible. Consequently, the user must ensure that only one transponder is present in the range of action of the read device.

SUMMARY

Therefore, an object of the present invention is to provide a specimen slide unit to hold a specimen that is to be examined under a microscope or analyzed with a laboratory analysis system, said specimen slide unit allowing the data carrier device to be read out or written quickly and unambiguously, even if several specimen slide units are arranged in close proximity to each other. It is an additional, alternative object of the present invention to provide a read/write device, communication and/or data transmission software and a microscope that are suitable for quickly and unambiguously writing on and/or reading out at least one data carrier device of a specimen slide unit. Additional, alternative object of the present invention are to provide a container to hold at least one specimen slide and/or at least one specimen slide unit, a method to examine a specimen under a microscope and/or to analyze a specimen with a laboratory analysis system and the use of a specific data carrier device for a specimen slide that is employed for microscopic analysis and/or for analysis with a laboratory analysis system in such a way as to avoid the above-mentioned problems.

The present invention provides a specimen slide unit for holding a specimen that is to be examined under a microscope or analyzed with a laboratory analysis system. The specimen slide unit includes: a specimen slide configured to receive the specimen; a data carrier device configured to be read out and/or written on in a contact-free manner by a read/write device, the data carrier device including a radio frequency identification tag (RFID tag) configured to be read out and/or written on using Phase Jitter Modulation so as to switch a communication carrier frequency between at least a first and a second predefinable communication carrier frequency; and a signal element activatable so as to assist an operator in following a predefinable processing sequence including a second specimen slide unit when the RFID tag is in a range of action of the read/write device and the specimen slide unit is next in the sequence, the signal element being at least one of a visual and an acoustic signal element.

BRIEF DESCRIPTION OF THE DRAWINGS

There are various ways in which to configure and refine the teaching of the present invention in an advantageous manner. The present invention will to elaborated upon below based on exemplary embodiments with reference to the drawings in which.

DETAILED DESCRIPTION

Figure 1:
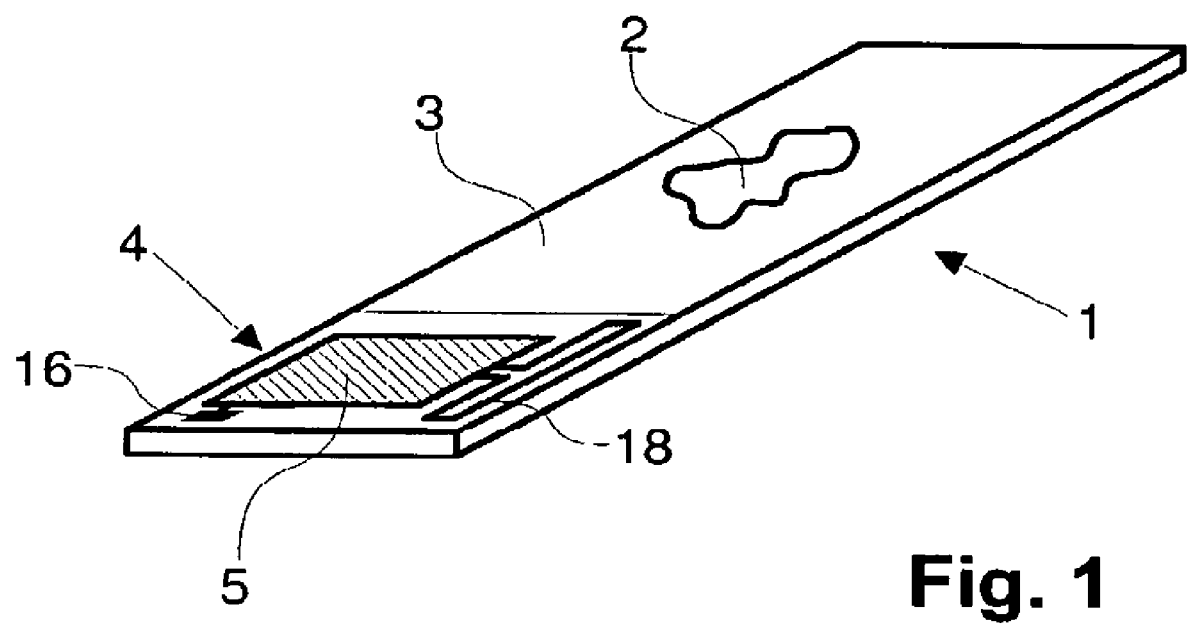
FIG. 1 a schematic depiction of an embodiment of the present invention.

According to the invention, it was recognized that data carrier devices based on RFID tags allow an unambiguous and reliable identification of even several specimen slide units since here—in comparison to the conventional transponders—measures to ensure unambiguous identification are taken in the RFID tag itself. Merely for the sake of providing an example, reference is hereby made to "RFID Handbuch" (RFID Handbook), published by Karl Hansa Verlag, $2^{nd}$ edition, Munich, Germany, 2000, authored by Klaus Finkenzeller, in which the RFID technology is described. Hence, in an especially advantageous manner, it is possible to use the specimen slide units in routine laboratory operations where specimen slides or specimen slide units are normally kept tightly packed in special containers and the containers of the specimen slides are often stacked in an unarranged manner next to or near an analysis system or microscope. Even if there are several specimen slide units in the range of action of a read/write device, an unambiguous identification of the various specimen slide units is always ensured. Ultimately, this makes it possible to enlarge the range of action of a read/write device in comparison to conventional transponder systems because the reading out or writing of several RFID tags in the range of action is possible since the individual RFID tags do not interfere with each other. Consequently, the throughput rate of microscopic preparations in laboratory operations can advantageously be increased, for example, by using a multi-preparation stage that can hold 4, 8, 16 or more specimen slide units. Moreover, it is a possibility to feed additional specimen slide units to the microscope as well as to the processing or analysis station using automatic, manual or semi-automatic change-over systems. Moreover, the reading and writing rate of the RFID tags is much faster than is the case with conventional transponders, namely, up to 25 times faster.

In an embodiment, the data carrier device is freely programmable. In this manner, the data carrier device can be written flexibly, for example, during a first writing procedure relating to the intended use so that, in an advantageous manner, an application-specific use of a specimen slide unit configured for various applications is possible. Thus, for instance, in the case of specimen slide units that are used for analysis with a laboratory analysis system, different data or information can be stored in the data carrier device of the specimen slide unit than, for example, would be the case with specimen slide units used in a laboratory where basic research is carried out by means of microscopic examinations.

Preferably, the data carrier device has a storage area and/or at least one instruction block. The storage area could contain the information pertaining to the specimen slide unit in question and/or to the appertaining specimen. This information could make it possible to unambiguously identify the specimen slide unit. In this context, such information could be stored as "read only" so that this information cannot be overwritten. In case of an automatic analysis of the specimen slide unit with a laboratory analysis system, the data carrier device could contain information in an instruction block about planned analysis steps of the individual processing stations of the laboratory analysis system. Accordingly, one's own processing program could be stored or computed in the data carrier device of a specimen slide unit, whereby this processing program can comprise information as to which processing stations of the laboratory analysis system and which mode are to be used to carry out the processing or analysis at each particular station.

In an embodiment, the RFID tag of a specimen slide unit can be read out and/or written on by means of Phase Jitter Modulation (PJM). Here, when the RFID tag is being read out and/or written on, the communication carrier frequency is switched between at least two—preferably eight—predefinable communication carrier frequencies. Such a switchover could take place constantly. As a result, in an advantageous manner, the reading or writing speed can be increased, which translates into a higher throughput rate for the analysis or examination of the specimen slide units according to the invention.

There are two types of PJM-RFID tags, namely, so-called item tags and so-called stack tags. On the one hand, the RFID tag could have an item tag. This makes it possible to determine the relative position of the RFID tag to a read/write device and thus to ascertain the spatial location of the specimen slide unit with a predefinable precision. This is useful especially if the positions of the specimen slide units change quickly and nevertheless have to be identified, or if the course of their positions over time has to be tracked, for example, in a laboratory analysis system. The RFID tag preferably has a type of antenna with which the position or location of the specimen slide unit can be ascertained with the highest level of precision possible. Thus, for example, the type of antenna with a dipole characteristic could be provided so that the RFID tag can be detected by means of an anisotropic detection field. On the other hand, the RFID tag could have a stack tag. With this, in particular, several specimen slide units—which are located spatially close to each other—can be identified almost simultaneously.

Fundamentally, it could be provided that information that identifies the specimen slide is stored in the data carrier device in order to allow a later unambiguous identification of the data carrier device and consequently of the specimen slide unit. This would preferably be done in such a way that the appertaining information cannot be deleted. The storage of this information in the data carrier device of a specimen slide unit could take place, for example, when the specimen is mounted on the specimen slide. Ideally, the information to be stored is unambiguous worldwide so that no other RFID tag with the same identification exists.

As an alternative or additionally, means could be provided in an RFID tag with which an RFID tag can be unambiguously identified. For this purpose, the RFID tag could have an unambiguous digital label stored in an appropriate storage area of the RFID tag. Preferably, the RFID tag can be unambiguously identified with the Electronic Product Code (EPC) standard, said Electronic Product Code defining a standard according to which unambiguous serial numbers are to be assigned. Normally, these serial numbers are generated and stored in the RFID tag by a manufacturer—for example, the manufacturer of the specimen slide units.

An unambiguous identification is also possible using the method described in German patent application DE 101 61 302 A1. Here, with the RFID tag located in the range of action of the read/write device, a random number and especially a test identification number are generated and supplied. The random number and, if applicable, the test identification number are transmitted to the read/write device. Then, on the basis of the random number and, if applicable, of the test identification number, the RFID tag can be unambiguously identified in the read/write device.

Preferably, the specimen slide unit could have a visual and/or an acoustic signal element. This could serve to assist an operator and could be activated in order to display to the operator a prescribed processing sequence for several specimen slide units if an RFID tag, together with the specimen slide unit, is in the range of action of the read/write device and this specimen slide unit is the next one that is to be processed or analyzed.

Finding a specific specimen slide unit could be facilitated in a similar manner. A visual and/or acoustic signal element could serve for this purpose as well, said signal element being activated if the specimen slide unit being sought or its RFID tag is in the range of action of the read/write device.

In an embodiment, the visual signal element could have a light emitting diode (LED) or another source of light that can be activated by an electronic circuit provided in the data carrier device. Especially preferably, this could be a multi-color LED that could light up in a different color as a function of certain analysis states. The energy supply for the signal element can be acquired from the electromagnetic field of the read/write device.

In a preferred embodiment, the data carrier device can be connected via the read/write device to a computer, to a data processing system and/or to a computer network. Here, a data record that belongs to the specimen slide can be stored on or is provided in the computer or in the computer network, said data record containing at least some of the data that is stored in the data carrier device of the specimen slide unit and/or other data that belongs to the specimen slide. Thus, for example, when the specimen is first mounted on the specimen slide, an appertaining data record relating to this specimen can be stored on the computer via a connection to the computer. In this process, an unambiguous marking or identification of the specimen slide could also be generated and stored in the data carrier device of the specimen slide unit and/or on the computer. In a later processing or examination step, the data record stored on the computer could be accessed, and for this purpose, the generated marking or identification allows access to an external database, to an expert system or to an external data record. An SQL server, for example, could serve as such a database. A linking with a patient database could be advantageous, for example, in a hospital since—assuming that an appropriate computer infrastructure is present—the results of a specimen examination in a laboratory could immediately be accessed by the consulting physician in a hospital ward.

A connection of the data carrier device to a computer network or to another network can advantageously allow improved telemicroscopy of the kind used, for example, in pathology. Here, the network—in the simplest case a telephone connection—would make it possible to obtain not only the image data of a specimen acquired with a microscope equipped with a camera but also data and information about the patient, the examined specimen and its preparation history. This data can be obtained from the data carrier device and/or from a data record stored on a computer. On the receiving side of the data transmission, a diagnosis could be made by another expert or pathologist either simultaneously or time-shifted.

In an advantageous manner, it is possible to store almost unlimited volumes of data pertaining to a specimen or to a specimen slide unit. Thus, for example, the data carrier device or the data record could especially contain information about processing steps that have been planned or completed for the specimen slide, about examination results or diagnosis results pertaining to the specimen and/or about image data of the specimen. For example, image data of the specimen might have been generated by a CCD camera connected to a microscope or by a confocal scanning microscope. Automatic image acquisition for applications in pathology is also conceivable. Owing to the different data structures—images, numbers, terms or names—a specimen-oriented database would be advantageous.

For instance, it can be provided that the data carrier device and/or the RFID tag are reversibly joined to the specimen slide for re-use. For this purpose, for example, the data carrier device or the RFID tag could be attached to the specimen slide magnetically, inserted, screwed in or else clicked in place with a snap fastener. A fastening of the data carrier device or of the RFID tag to the specimen slide by means of Velcro is likewise conceivable. Consequently, the data carrier device can advantageously be employed again for another specimen slide once the used specimen slide is no longer needed and is thus thrown away. A reversible joining of the data carrier device and/or of the RFID tag to the specimen slide is especially useful in the realm of basic research, particularly if examination under a microscope has shown that an experiment was unsuccessful.

As an alternative, it can be provided that the data carrier device and/or the RFID tag can be irreversibly joined to the specimen slide. A riveted, glued or press-formed attachment is especially suitable here. This fastening technique is especially conducive for applications in which person-related or patient-related specimens are the subject of microscopic examinations or laboratory analyses. Often, in this case, the specimens have to be archived for a prolonged period of time, during which unauthorized manipulation at least of the specimen slide unit has to be largely ruled out. Ultimately, the irreversible joining of the data carrier device or of the RFID tag to the specimen slide unit prevents the information stored in the data carrier device of the specimen slide unit from being removed from the specimen slide and being lost.

In an embodiment, the data carrier device can be protected against an unauthorized reading and/or writing procedure. This is preferably achieved by encrypted storage of the data in the data carrier device, especially by means of cryptological methods. In addition or as an alternative, such precautions could be implemented in an instruction block of the data carrier device, for example, in the form of a password query. Such a password query is easy to realize, especially if the data carrier device or the RFID tag is connected to a computer and the password query can be processed via the computer keyboard. Thus, generally speaking, a password query could be provided for purposes of authorized reading out and/or writing of the data of the data carrier device. The same applies to the data transmission between the RFID tag and the read/write device by radio in conjunction with unauthorized intercepting or listening. Here, again, comparable protection mechanisms could be put in place.

As a matter of principle, conventional electric memory chips or the data carrier device are susceptible to damage under the conditions that prevail in a laboratory. They can be exposed to the effects of water, mild alkaline solutions or acids or to corrosion that can attack, for example, the contacts of the electric memory chips, as a result of which reliable operation over the long run is not ensured.

In order for the specimen slide unit to be used in routine laboratory operations, the data carrier device could be configured in such a way that it is temperature resistant. The temperature resistance could be provided especially for the temperature range from −40° C. to 150° C. [−40° F. to 302° F.]. Moreover, the data carrier device could be resistant to water, alkaline solutions and/or acids, as a result of which the specimen slide unit—and hence also the data carrier device—can advantageously undergo conventional specimen staining procedures. Particularly if a specimen slide unit is supposed to be used for another specimen, it is advantageous if the data carrier device is made so that it can be autoclaved. Such a resistance could be achieved, for example, by applying appropriate coatings to the data carrier device and/or to the RFID tag.

A read/write device according to the invention is characterized in that a specimen slide unit according to the invention can be read out and/or written on. In the simplest case, this read/write device could be a free-standing device that can be connected to a computer or network via a cable connection to a computer interface, for example, to a serial, parallel or USB interface, or else via a WLAN connection (Wireless Local Area Network) or Bluetooth or Firewire.

Consequently, a read/write device according to the invention can be introduced into an already existent laboratory simply and cost-effectively, so that advantageously, there is no need for a comprehensive adaptation or retooling of the laboratory equipment already present there. The read/write device according to the invention could also be a module of a laboratory device or of a microscope. Already existent microscopes and laboratory equipment could be retooled or adapted to a specimen slide unit according to the invention by replacing the appertaining module of the laboratory device or microscope. Consequently, upgrading and retooling can be achieved cost-effectively.

Preferably, the read/write procedure and/or the evaluation procedure of the data carrier device are software-controlled. Thus, for example, existing components of the read/write device according to the invention can be updated at a later point in time to have new functionalities so that no new hardware has to be purchased for updating purposes.

In an embodiment, the range of action—within which a specimen slide unit can be read out and/or written—of a read/write device according to the invention can be predefined or varied. Normally, the range of action is about 1 to 2 meters. Preferably, the predefinable range could be set as a function of the circumstances in a laboratory environment so that specimen slide units can only be read out or written in given areas of the laboratory environment.

The data transmission between a data carrier device and a read/write device or else between a read/write device and a computer or network could take place by means of the Bluetooth or the WLAN (Wireless Local Area Network) standard or Firewire. These are standards that are well-established in the computer realm, so that the connection to computers or computer networks can be made with very little technical effort.

The deletion of the stored content of the data carrier device or of the RFID tag could be carried out by means of an—especially software-controlled—routine. The deletion procedure could be logged in an appertaining data record that is stored in a computer, in a data processing system and/or in a computer network. For this purpose, a security question could be provided so as to largely prevent unintentional deletion of one or more RFID tags.

Moreover, the read/write device according to the invention could be configured as a portable device so that an operator can take it along. This would make it possible to find a specific specimen slide unit, for example, in a laboratory with several rooms. For this purpose, it is advantageous for the specimen slide units to be configured with the above-mentioned signal element.

Software according to the invention is characterized in that it is used for communication and/or data transmission between a data carrier device of a specimen slide unit according to the invention and a read/write device according to the invention. In particular, it could be provided that the software according to the invention can run on various platforms. Thus, a version of the software could be provided on various hardware platforms such as, for instance, conventional personal computers (PCs), tablet PCs, pocket PCs (PDAs), microchips, PGAs (Programmable Gate Array) and/or multifunctional cell phones. The software can preferably be implemented on different operating systems, especially for Windows, Macintosh, Unix, Linux and/or Java. Especially preferably, integration into special (industry) software solutions is provided, for example, into SAP-RFID.

Preferably, the software is an interface to an Object Name Service (ONS) with which the Electronic Product Code (EPC) can be associated with a specimen slide unit and/or with which predefinable services—preferably via the Internet/Intranet—can be linked and/or accessed. In this manner, for example, certain services or websites could be resolved/translated or accessed on the basis of the EPC numbers. The ONS is comparable to the Domain Name Service System used for the resolution of web addresses on computer numbers (IP numbers).

A microscope according to the invention is characterized by a read/write device according to the invention, which cooperates with the microscope and by means of which a specimen slide unit according to the invention can be read out and/or written.

With the microscope according to the invention, in a likewise advantageous manner, during a microscopic work procedure, data or information from the data carrier device of a specimen slide unit according to the invention can be read out, optionally processed by a computer and changes can be stored once again in the data carrier device. Automatically or through interaction with a microscope operator, the microscope can be used to temporarily store analysis-relevant data or to retrieve it from the data carrier device of the specimen slide unit simultaneously during the microscopic analysis. In this process, the data from a specimen slide unit according to the invention can be read out by means of the read/write device, and said data can then be applied in an analysis process and can be written back onto the specimen slide unit according to the invention by means of the read/write device. Here, the read/write device—depending on its range of action—can also be arranged in the immediate vicinity of the microscope; in other words, it does not have to be a permanent part of the microscope. Accordingly, a cooperation between the read/write device and the microscope is to be understood to the effect that a direct or indirect connection is provided between the two devices. The read/write device can be adapted to the microscope or connected to it, for example, via a network connection.

Preferably, the read/write device is arranged on the microscope or in its immediate vicinity. In a concrete case, the read/write device could be arranged on the microscope stage or on the stand of the microscope.

In an embodiment, the position of at least one specimen slide unit relative to the microscope can be determined by means of the read/write device. For this purpose, RFID tags could be used that have an item tag and/or the configuration of the type of antenna of the RFID tag could be such that the location of the specimen slide unit can be determined with extremely high precision. Especially if specimens on several specimen slide units have to be analyzed or examined in laboratory operation, it can be necessary to know where individual specimen slide units are located. This applies especially to a multi-preparation stage on which 4, 8, 16 or more specimen slide units are arranged at the same time and which are to be examined under the microscope consecutively. Thus, a determination of the location of the individual specimen slide units on the microscope stage is helpful in such a case. There might be a need for the precision of the position determination of a specimen slide unit to be better than 1 cm.

Preferably, the position of a specimen slide unit relative to the microscope could be determined as follows: the specimen slide unit has a visual signal element that could be activated if the specimen slide unit in question is being sought and therefore its position relative to the microscope is to be determined. At least one light-sensitive detector is provided on the microscope, for example, on a motorized microscope stage. The light-sensitive detector can detect only the light emitted by the activated visual signal element. Then the microscope stage could be moved into a prescribed position once the sought specimen slide unit had been found, for example, in order to automatically acquire an image under the microscope lens. This could be especially advantageous if several specimen slide units are present on the microscope stage and it is a multi-preparation stage, so to speak. The light-sensitive detector could have, for example, a photodiode.

Preferably, the specimen slide unit examined under the microscope can be marked as the specimen slide unit that is actively being processed. Such an activation could be effectuated visually on the specimen slide unit, for example, by means of a signal element—already mentioned—so that, for instance, an operator can check which of the specimen slide units is currently being processed. A specimen slide unit that is being processed is preferably also marked as such in a database or in a computer, said database or computer being connected to the microscope and/or to the specimen slide unit. The activation can be used to log the examinations of the specimen slide units, for example, in a laboratory control program.

In particular, it could be provided that a mode of operation of the microscope that is suitable for examining a specimen is automatically set and/or is suggested to the operator on the basis of the information stored in the data carrier device of the specimen slide unit. In this manner, for example, it is possible for the microscope to assume a specific microscopic operating state. Here, a microscope is capable of recognizing and executing a certain mode of operation or a certain microscopy process desired by the operator such as, for example, a phase contrast method or a microscopy method that is practical for examining the specimen. The microscope then automatically adjusts itself for the phase contrast method, that is to say, all of the relevant microscope parameters are automatically set in such a way that the user can work with phase contrast at the push of a button, so to speak. Conceivable modes of operation include transmitted light, reflected light, dark field or fluorescence, interference contrast or phase contrast. Accordingly, in addition to the already mentioned microscope parameters, the following can also be set automatically:

camera settings along with appertaining filter wheel positions and/or exposure times, wavelength-relevant settings of the microscope imaging, for example, filter cubes, filter wheel positions, monochromatic illuminator settings and/or laser wavelengths of a confocal scanning microscope, other microscope settings, for example, Köhler illumination systems, diaphragm positions, pinhole diameters of a confocal scanning microscope, stage position (X, Y, Z) of a motorized microscope stage, settings of all other peripherals (piezo focus, shutters, etc.), triggers for external components, transmission of information about the operating state or about a change in the operating state to a central control or monitoring unit for (server) quality assurance.

If data is sent to the microscope by an external storage unit, for example, by the specimen slide fitted with an RFID tag, or by another type of data transmission for purposes of automatically switching over the method or mode of operation as a function of the preparation, it can be achieved that the microscope automatically adjusts itself to the method or mode of operation with which the specimen slide is to be examined when said specimen slide with a data carrier device according to the invention or an RFID tag is put in place. In this manner, at least some—if not all—work steps can be automated, thereby advantageously shortening the duration of the examination. A possible mode of operation of the microscope can be suggested to an inexperienced microscope operator—for example, on a display provided on the microscope—and, after confirmation by the operator, this mode of operation could be automatically established. Thus, the operation of the microscope is greatly simplified and setting errors on the part of an operator are avoided—errors that can damage the specimen, for example, the bleaching out of a fluorescent dye used to mark the specimen.

Moreover, in an advantageous manner, this measure improves the ergonomics for a user and thus reduces errors. The learning curve for an inexperienced microscope operator can advantageously be shortened. Moreover, this makes full automation possible for one or more consecutive examinations with the microscope, and the fully automatic microscope—depending on the desired degree of automation—could have a motor-driven lens turret for automatic lens changing, motor-driven filter blocks and/or a motor-driven microscope stage. If the microscope settings established during an examination of a specimen slide are stored in the data carrier device or in the RFID tag, on the one hand, a repeat examination of the same specimen slide or specimen/preparation can be carried out under virtually the same conditions even years after the examination and, on the other hand, the examination steps and methods that were used with the microscope can be reconstructed.

In an embodiment, the microscope is configured in such a way that it can be automatically adjusted using the information stored in the data carrier device of the specimen slide unit. This could include, for example, the setting of the illumination strength, of a diaphragm diameter or of a camera. An automatic "coarse focusing" of the specimen slide could be carried out, for example, in that the RFID tag is imaged several times at different focus settings using a CCD camera adapted to the microscope. The acquired images could then be compared to the expected image of the RFID tag and/or examined by means of digital image processing methods, for example, to ascertain their imaging sharpness. Then, the coarse focus that is selected is the focus setting that corresponds to the one at which the image with the best results was acquired. The prerequisite for this is that the RFID tag and the specimen have to be arranged in the same plane on the specimen slide unit or else they have to have a known relationship in terms of their position relative to each other along the optical axis. It is also conceivable for other processing steps to be carried out automatically such as, for example, automatically searching the specimens present on the specimen slide and selectively storing the acquired image data.

A laboratory analysis system according to the invention with several processing and/or analysis stations is characterized by at least one read/write device with which a specimen slide unit according to the present invention can be read out and/or written on. The specimen slide unit, along with the RFID tag, comprises a process-accompanying information carrier that is transported with the specimen slide unit to the individual processing and/or analysis stations. On the basis of the data about the specimen that is stored in the RFID tag, the specimen or the specimen slide unit can be identified in each processing station by means of a read/write device. Moreover, information could be stored in the RFID tag indicating which processing and/or analysis steps are to be performed on the specimen of the specimen slide unit in question.

Preferably, the laboratory analysis system according to the invention is a laboratory robot system with which specimen slide units according to the invention are taken to individual analysis stations as they undergo various analysis steps, at least partially using a robot system. Such laboratory analysis systems are used, among other things, in pathology, where a large number of specimen slide units and their associated specimens are processed, some with different staining methods, automatically analyzed and evaluated.

Preferably, the processing and/or analysis steps required for the specimen can be determined automatically and/or with operator assistance on the basis of the data present in the data carrier device. This is especially provided for laboratory analysis systems with different processing and/or analysis sequences, where several specimen slide units undergo different processing steps or can automatically follow different processing routes.

Preferably, the completed processing steps can be logged and/or stored and/or—preferably in real time—monitored in the RFID tag and/or in an external database. In this manner, high process automation, along with high process reliability, can be achieved so that a laboratory analysis system with a high reliability can be attained.

A container according to the invention can hold at least one specimen slide and/or at least one specimen slide unit, said specimen slide having specimens that are to be examined under a microscope and/or analyzed with a laboratory analysis system. The container has a data carrier device that can be read out and/or written on by a read/write device. The container according to the invention is characterized in that the data carrier device has an RFID tag. As a result, for example, several conventional specimen slides and/or specimen slide units according to the present invention can be kept in a container according to the invention and stored for a prolonged period of time, making it easy to find a specific specimen slide on the basis of the information stored in the data carrier device. The container can especially serve to transport several specimen slides or specimen slide units.

A method according to the invention is characterized in that the specimen is mounted on a specimen slide unit according to the invention. The mounting of a specimen on a specimen slide unit can comprise the mounting of a specimen on a conventionally configured glass specimen slide of a specimen slide unit. According to the invention, the specimen is accompanied by a specimen slide unit during the examination and/or analysis or, if applicable, already during the preparation work that precedes the examination or analysis, and information about the specimen is stored in the data carrier device and, during each processing step, it is available and/or can be stored in the data carrier device.

For this purpose, information is preferably stored in the data carrier device about processing steps that have been planned or completed for the specimen slide, about examination results or diagnosis results pertaining to the specimen and/or about image data of the specimen, so that a specimen slide unit knows its own "processing history" and/or the processing steps provided for an analysis. This information is used for processing or examining the specimen.

The use of an RFID tag according to the invention for a specimen slide unit that is used for microscopic analysis and/or for analysis with a laboratory analysis system entails many advantages, which will be elaborated upon below:

Contact-free identification—in less than 1 second—of the specimen slide unit even without visual contact—unlike with infrared connections—is also possible through various materials such as, for example, cardboard or wood, so that sturdy use in microscopy is possible. Reading out and/or writing on the data carrier device or the RFID tag can be carried out as often as desired. If necessary, several specimen slide units can be identified, read out and/or written on at the same time. The shape and size of an RFID tag can be adapted to or integrated into a specimen slide as desired. An RFID tag is normally resistant to environmental influences, which can also include extreme temperatures, moisture, acids, fluorochromes. An RFID tag cannot be deleted by a permanent magnet. The RFID tag can be completely integrated into a specimen slide and is inexpensive to manufacture.

Figure 2:
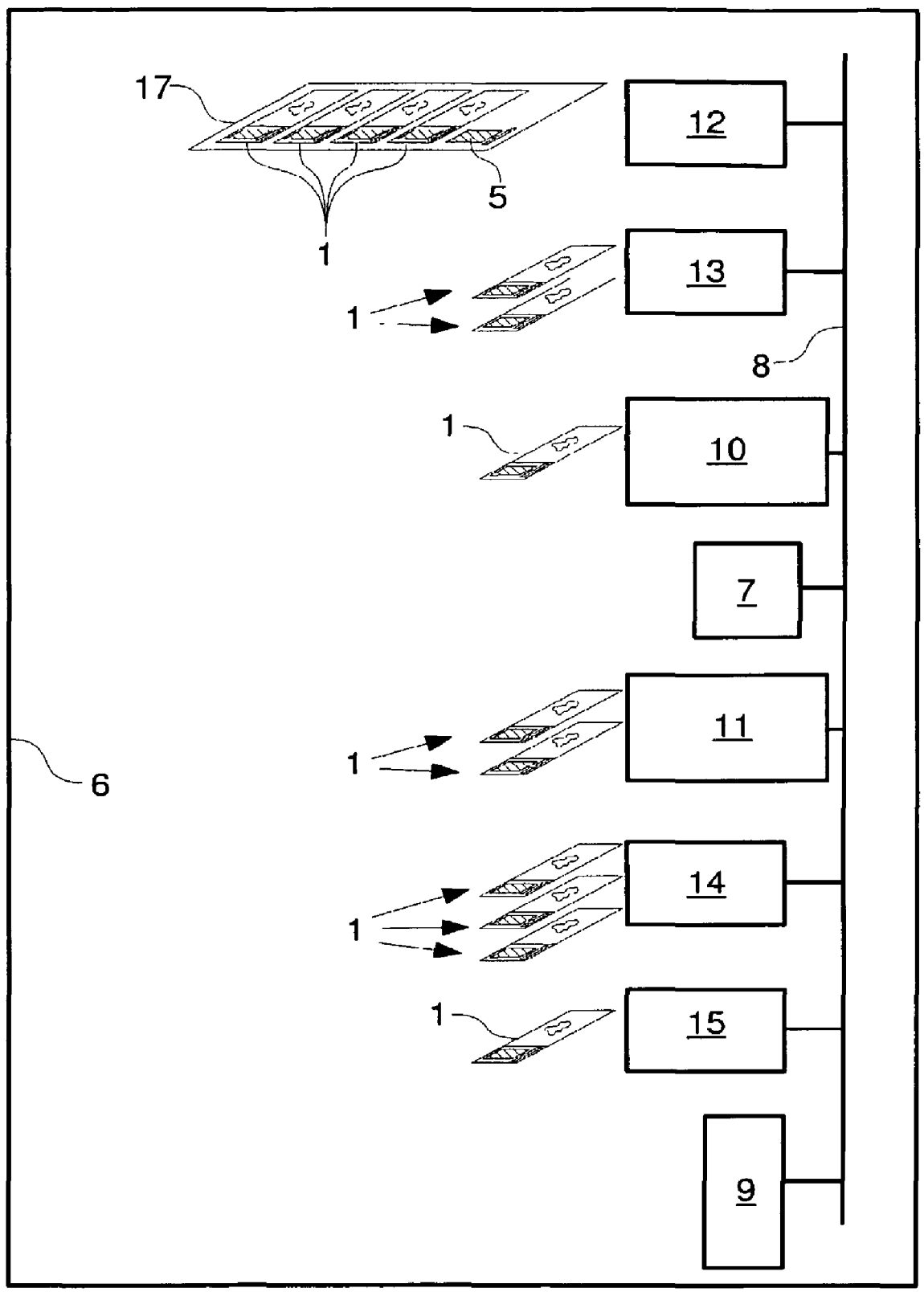
FIG. 2 a schematic depiction of a second embodiment of the present invention.

Identical or similar components that are shown in FIGS. 1 and 2 are designated with the same reference numerals. FIG. 1 shows a specimen slide unit 1 to hold a specimen 2. The specimen 2 is a histological section that is to be examined pathologically under a microscope that is not shown in FIG. 1. The specimen 2 is held in a specimen slide 3 that is configured in the form of a conventional glass slide. Moreover, the specimen slide unit 1 includes a data carrier device 4 in which data and information about the specimen 2 can be stored.

According to the invention, the specimen slide unit 4 has an RFID tag 5 or the specimen slide unit 4 is configured in the form of an RFID tag 5. In the RFID tag 5, information is stored that identifies the specimen slide 3, that cannot be deleted and that permits an unambiguous identification of the specimen slide 3. The data carrier device 4 is irreversibly joined to the specimen slide 3.

FIG. 2 shows a laboratory room 6 in which several preparation and analysis devices are operated. In the laboratory room 6, a read/write device 7 is provided, by means of which the specimen slide units 1 that are likewise in the laboratory room 6 can be read out and/or written on. The read/write device 7 is connected via a network 8 to, among other things, the control computer 9 or else to other laboratory rooms—not shown in the figure. Consequently, the read/write device 7 is controlled by the control computer 9 when it is reading out and/or writing. Moreover, two microscopes 10, 11 are present in the laboratory room 6, microscope 10 being a conventional research microscope and microscope 11 being a confocal scanning microscope. Furthermore, processing stations 12 to 15 are provided with which the specimens 2 associated with the specimen slide units 1 can be prepared. The processing station 12, 13 is a microtome and the processing station 14, 15 is an automatic staining system.

The microscopes 10, 11 as well as the processing stations 12 to 15 are connected to the network 8. The figure merely schematically indicates that four specimen slide units 1 are being processed in the processing station 12, two specimen slide units 1 are being processed in the processing station 13 and in the microscope 11, one specimen slide unit 1 is being processed in the microscope 10 and in the processing station 15, whereas three specimen slide units 1 are being processed in the processing station 14.

The range of action of the read/write device 7 is dimensioned in such a way that, on the one hand, all of the specimen slide units 1 present in the laboratory room 6 can be read out and/or written on and, on the other hand, that their position can be determined with sufficient precision. The laboratory 6 according to FIG. 2 is configured for manual operation, that is to say, an operator transfers the individual specimen slide units 1 to and from the processing stations 12 to 15 or to the microscopes 10, 11 and performs the data acquisition at the microscopes 10, 11.

Each specimen slide unit 1 comprises a signal element 16 configured in the form of an LED shown in FIG. 1. This signal element 16 can be activated in various situations and can be multicolored so that it is able to display different signal states, for example, when a specific specimen slide unit 1 is being sought in the laboratory room 6. The signal element 16 of a specimen slide unit 1 could also be activated while it is being actively processed by a processing station 12 to 15. Moreover, each data carrier device 4 or each RFID tag 5 has an antenna 18 that serves to transmit data and electric energy between the RFID tag 5 and the read/write device 7.

At the processing station 12, four specimen slide units 1 are accommodated in a container 17, which has its own RFID tag 5. Consequently, the container 17 can also be identified and located by the read/write device 7 and can be read out by it and/or written with data.

Finally, it should be explicitly pointed out that the embodiments explained above serve only to describe aspects of the claimed teaching, but the latter is not limited to these embodiments.

LIST OF REFERENCE NUMERALS 1 specimen slide unit
2 specimen
3 specimen slide
4 data carrier device
5 RFID tag
6 laboratory room
7 read/write device
8 network
9 control computer
10 research microscope
11 confocal scanning microscope
12 microtome
13 microtome
14 automatic staining system
15 automatic staining system
16 signal element
17 container
18 antenna

The invention claimed is:

1. A specimen slide unit for holding a specimen that is to be examined under a microscope or analyzed with a laboratory analysis system, the specimen slide unit comprising:
a specimen slide configured to receive the specimen;
a data carrier device configured to be read out and/or written on in a contact-free manner by a read/write device, the data carrier device including a radio frequency identification tag (RFID tag) configured to be read out and/or written on using Phase Jitter Modulation so as to switch a communication carrier frequency between at least a first and a second predefinable communication carrier frequency; and
a signal element disposed on the specimen slide unit, the signal element activatable to emit at least one of a visual and an acoustic signal so as to assist an operator in following a predefinable processing sequence including a second specimen slide unit when the RFID tag is in a range of action of the read/write device and the specimen slide unit is next in the sequence, the signal element being at least one of a visual and an acoustic signal element.

2. The specimen slide unit as recited in claim 1 wherein the RFID tag is configured to be read out and/or written on using Phase Jitter Modulation so as to constantly switch the communication carrier frequency between the at least first and second predefinable communication carrier frequencies.

3. The specimen slide unit as recited in claim 1 wherein the RFID tag includes an item tag, a position of the item tag being determinable relative to the read/write device so as to determine a spatial location of the specimen slide unit with a predefinable precision.

4. The specimen slide unit as recited in claim 1 wherein the RFID tag includes an antenna configured to determine a position or location of the specimen slide unit with a predefinable level of precision.

5. The specimen slide unit as recited in claim 4 wherein the antenna has a dipole characteristic.

6. The specimen slide unit as recited in claim 1 wherein the RFID tag includes a stack tag configured to almost simultaneously identify the specimen slide unit and the second specimen slide unit.

7. A specimen slide unit for holding a specimen that is to be examined under a microscope or analyzed with a laboratory analysis system, the specimen slide unit comprising:
a specimen slide configured to receive the specimen;
a data carrier device configured to be read out and/or written on in a contact-free manner by a read/write device, the data carrier device including a radio frequency identification tag (RFID tag) configured to be read out and/or written on using Phase Jitter Modulation so as to switch a communication carrier frequency between at least a first and a second predefinable communication carrier frequency; and
a signal element disposed on the specimen slide unit, the signal element activatable to emit at least one of a visual and an acoustic signal so as to locate the specimen slide unit when the RFID tag is in a range of action of the read/write device, the signal element being at least one of a visual and an acoustic signal element.

8. The specimen slide unit as recited in claim 7 wherein the data carrier device includes an electronic circuit, and wherein the signal element includes a visual signal element having a light source activatable by the electronic circuit.

9. The specimen slide unit as recited in claim 8 wherein the light source includes a light emitting diode.

10. The specimen slide unit as recited in claim 8 wherein the light source is activatable in a plurality of colors.

11. The specimen slide unit as recited in claim 7 wherein the data carrier device is configured to store first data and is connectable via the read/write device to a computing system so as to store or provide a data record of the specimen slide on the computing system, the computing system including at least one of a computer, a data processing system and a computer network, the data record including at least one of a portion of the first data and second data relating to the specimen slide.

12. The specimen slide unit as recited in claim 11 wherein the data record is at least one of storable in and accessible from a patient database.

* * * * *